United States Patent
Finidori

(10) Patent No.: US 6,761,879 B1
(45) Date of Patent: Jul. 13, 2004

(54) TITANIUM DERIVED COMPOUNDS, PREPARATION AND USE THEREOF

(75) Inventor: Claudine Finidori, Oveilly (FR)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 10/031,087

(22) PCT Filed: Jul. 11, 2000

(86) PCT No.: PCT/FR00/01994

§ 371 (c)(1),
(2), (4) Date: Apr. 17, 2002

(87) PCT Pub. No.: WO01/05797

PCT Pub. Date: Feb. 25, 2001

(30) Foreign Application Priority Data

Jul. 16, 1999 (FR) .......................................... 99 09194

(51) Int. Cl.$^7$ .............................. A61K 7/16; C07F 7/28
(52) U.S. Cl. ............................................. 424/49; 556/54
(58) Field of Search .............................. 424/49; 556/54

(56) References Cited

PUBLICATIONS

Dean, Philip A. W. et al: "Spectroscopic studies of inorganic fluoro complexes. III. Fluorine–19 nuclear magnetic resonance studies of silicon (IV), germanium(IV), and titanium(IV) fluoro complexes"; J. Chem. Soc. A (1970), (15), pp. 2569–2574.

*Primary Examiner*—Porfirio Nazario-Gonzalez
(74) *Attorney, Agent, or Firm*—Paul E. Dupont; Michael D. Alexander

(57) ABSTRACT

The invention relates to a titanium-derived compounds, and to processes for preparing the same.

32 Claims, No Drawings

TITANIUM DERIVED COMPOUNDS, PREPARATION AND USE THEREOF

The invention relates to novel titanium-derived compounds, as well as to the preparation thereof.

The invention also relates to compositions for buccal use comprising such titanium-derived compounds.

It is known that titanium tetrafluoride (TiF$_4$) can bind to the surface of the tooth, forming an amorphous protective layer, also termed glaze, at the surface of the enamel of the tooth.

The formation of such a protective layer at the surface of the tooth has led to envisage the use of titanium tetrafluoride as an agent for preventing and for treating dental caries.

Titanium tetrafluoride has however the drawback of being highly acidic in aqueous solution (pH of about 1.5), which is aggressive for the tissues mineralized and not compatible with physiological pHs.

Its use in preventing dental caries has thus been limited, so far, to professional use with a very short application time, followed by rinsing.

Titanium tetrafluoride also has the drawback of being relatively unstable, in particular in aqueous solution.

The aim of the invention is to remedy these drawbacks by providing titanium IV-derived compounds comprising fluorine which are capable of forming a glaze at the surface of the tooth, and which can be used in aqueous solution and at physiological pHs varying from approximately 6.5 to approximately 7.5.

The titanium-derived compounds according to the invention satisfy the formula (I) below:

$$[TiF_xL_y]^{z-} \qquad (I)$$

in which L represents a compound of formula (II) below:

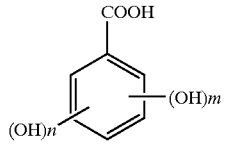

(II)

in which m is 0 or 1 and n is 0, 1 or 2, and x represents 2, 4 or 5 y represents 1 or 2 and z represents 0, 1 or 2.

The compounds of formula (I) can comprise one or more asymmetrical carbon atoms. They can thus exist in the form of enantiomers or of diastereoisomers. These enantiomers and diastereoisomers, as well as the mixtures thereof, including the racemic mixtures, form part of the invention.

The compounds of the present invention can exist in the form of free bases or of addition salts to pharmaceutically acceptable acids. All these forms form part of the invention.

According to the invention, compounds L which can be used are in particular benzoic acid derivatives, in particular 2-hydroxybenzoic acid of formula:

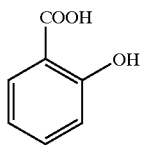

3-hydroxybenzoic acid of formula:

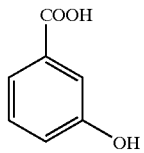

4-hydroxybenzoic acid of formula:

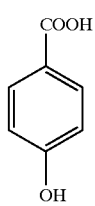

2,3-dihydroxybenzoic acid of formula:

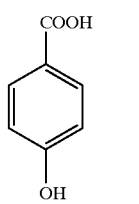

3,4-dihydroxybenzoic acid of formula:

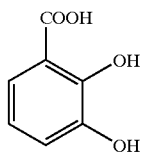

An example of a titanium-derived compound according to the invention is the compound represented by the formula below (III):

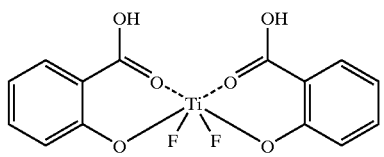

(III)

The titanium(IV)-derived compounds of the invention can be prepared by reacting, at room temperature; solid titanium IV fluoride with a solution of benzoic acid in an anhydrous solvent such as acetonitrile, under a nitrogen atmosphere.

The starting products are commercially available or described in the literature, or can be prepared by methods which are described therein or which are known to persons skilled in the art.

The invention is also directed towards protecting compositions for buccal use comprising at least one compound according to the invention, and also the use of the titanium-derived compounds according to the invention, as a protecting agent against dental caries.

The compositions of the invention comprise at least one compound according to the invention in an amount which is equivalent to from approximately 10 ppm to approximately 10,000 ppm of fluorine, and which is calculated from the molecular weight of the compound according to the invention.

The compositions of the invention can be in the usual diverse forms for compositions for buccal use, and in particular in the form of toothpaste or toothgel, of mouthwash, of spray, of foam, of gargling product, of dental gel or of chewing gum, balm, paste, glaze, lozenge, tablet, antiseptic throat preparation, powder, or concentrated or unconcentrated solution, the vehicle therefore being chosen depending on the form of use desired.

The compositions of the invention can contain, in addition to the titanium-derived compound(s), by way of vehicle or for their intrinsic activity, excipients or ingredients usually used in compositions for buccal use.

The compositions of the invention are prepared according to the usual methods which correspond to the vehicles chosen. The physiologically acceptable vehicle can be different in nature depending on the form chosen for the composition: aqueous solution, thickened or unthickened aqueous-alcoholic solution, gum, pasty or solid excipient, etc.

According to the forms desired, the compositions of the invention can also comprise at least one polishing agent in proportions ranging up to 80% by weight with respect to the total weight of the composition. The polishing agents are for example of inorganic or organic origin. Their nature may differ according to the vehicle used for the chosen form.

Polishing agents which can be used comprise calcium, magnesium or sodium carbonate or bicarbonate, calcium phosphates and sulphates, alumina and hydrated alumina, silicas, magnesium or calcium oxides, hydroxides, trisilicateis and pyrophosphates, or cellulose compounds obtained by crushing cereal seeds for example.

When the compositions are in the form of toothpaste, they can contain a polishing agent in proportions generally of between approximately 2% and approximately 70% by weight, preferably of between approximately 15% and approximately 25% by weight. It is generally an inorganic abrasive polishing agent consisting of one or more compounds which are, for the most part, insoluble in water. By way of examples, mention may be made of sodium or potassium metaphosphates, calcium phosphate dihydrate, dicalcium phosphate, tricalcium phosphate, calcium pyrophosphate, alumina, hydrated, and in particular trihydrated, aluminas, silicas, aluminium or zirconium silicates, bentonite, as well as magnesium orthophosphate or trimagnesium phosphate, and calcium or sodium carbonates and bicarbonates.

The compositions of the invention which are in the form of toothpaste can also comprise one or more cohesion agents. Such cohesion agents can be incorporated in proportions ranging up to approximately 10% by weight with respect to the total weight of the composition, and preferably of between approximately 0.5% and approximately 3% by weight. The cohesion agents can be chosen in particular from natural thickeners such as alginates or pectins, natural gums such as gum tragacanth or xanthan, guar, carob or carrageenan gums, and synthetic thickeners such as cellulose derivatives for instance the sodium salt of carboxymethylcellulose, methycellulose, hydroxyalkylcelluloses, crosslinked polyacrylic acids or synthetic carrageenates.

According to certain embodiments, the compositions of the invention can comprise one or more sufficiently stable and foam-forming surfactants. The surfactants which can be used may be of, anionic, amphoteric, zwitterionic, cationic or nonionic nature.

Generally, the surfactants are present in the compositions of the invention in a weight range which varies from approximately 0.01% to approximately 4%, preferably from approximately 0.1% to approximately 2%, with respect to the total weight of the composition.

In addition, the compositions of the invention can comprise other active agents which are used in buccal hygiene, in particular agents known to reduce bad breath, such as for example cyclodextrins or zinc compounds such as for example zinc halides, zinc acetate, zinc citrate or zinc fluoride, chlorhexedine or cetylpyridinium chloride.

The compositions of the invention can also comprise diverse cohesion agents, thickeners, antibiotics, sweetening, wetting or refreshing agents, peptizing agents, preserving agents, sweeteners, dyes, aromas, flavourings and flavour-enhancing substances, plasticizers, antibacterial agents or bactericides, vitamins, antitartar agents, healing agents, vasomotor agents, anti-bleeding agents, agents which are active on the gums, anti-inflammatory agents such as enoloxone, benzydamine, allantoin; permethol, etc.

These various agents are present in the compositions of the invention according to the form of use.

Thus, when the composition for buccal use is a spray, the vehicle can be an aqueous-alcoholic solution, and the composition can also comprise aromas, peptizing agents, and sweetening, wetting or refreshing agents.

When the composition for buccal use is in the form of mouthwash, the vehicle can be nonaqueous, aqueous or aqueous-alcoholic with one or more surfactants and/or one or more thickeners, and can also comprise bactericidal agents, sweetening agents and flavourings.

By way of example, when the composition is in the form of dental gel, it can also comprise agents which are active on the gums.

When the composition is in the form of chewing gum, it comprises at least one natural or synthetic chewable gum, and can also comprise plasticizers, vitamins, flavourings or flavour enhancers, sweeteners, wetting agents, bactericides, preserving agents, dyes.

Among the chewable gums which can be used are in particular hevea latex, chicle gum, schlong gum, polyvinyl acetate and synthetic elastomers, in particular silicone rubber, butyl rubber and the derivatives and/or mixtures thereof.

The compositions for buccal use of the invention can also comprise a sweetening agent. Among the sweetening agents which can be used, mention may be made of sucrose, lactose, fructose, xylitol, sodium cyclamate, sodium saccharinate or maltose, sodium or ammonium glycyrrhizinates, alpha-glucosyl/steviolglucoside mixtures, D-mannitol, aspartame, acesulfame K, sorbitol, lycosin and mixtures thereof.

The sweetening agents are generally present in an amount ranging up to approximately 2% by weight with respect to the total weight of the composition.

As wetting agents, mention may be made of sorbitol, glycerol or xylitol, which are present as such in concentrations which can reach 70% by weight.

In addition, refreshing agents such as menthol or ethylmaltol can be incorporated into the compositions of the invention.

It is also possible to use preserving agents, which are chosen from in particular methyl parahydroxybenzoate, propyl parahydroxybenzoate, sodium benzoate and chlorhexedine, at concentrations generally of approximately 1% by weight or lower.

The flavourings which can be used comprise all those which are authorized as such in the food trade. For example, mention may be made of mint, aniseed, eucalyptus, cinnamon, clove, sage and liquorice essences, and fruit essences such as orange, lemon, mandarin or strawberry. The flavourings are generally present in an amount by weight of approximately 5% or less.

The compositions of the invention can also comprise an antibacterial agent chosen preferably from in particular essential oils, plant extracts or substances such as cetylpytidinium chloride, alexidine, octinidine, hexetidine, phenoxyethanol, phenethyl alcohol, triclosan, chlorhexidine, cetylpyridinium chloride and delmopinol, in proportions ranging up to approximately 10% by weight with respect to the total weight of the composition.

The example which follows illustrates the preparation of a titanium-derived compound of the invention. The elemental microanalyses and the I.R. and N.M.R. spectra confirm the structure of the compound obtained.

EXAMPLE 1

Preparation of the compound of formula (III):

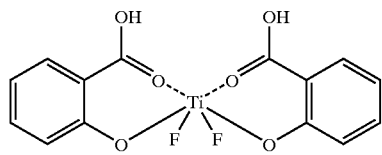

5 g (0.040 mol) of solid titanium fluoride are added to 10 g (0.072 mol) of asalicylic acid solution in 100 ml of anhydrous acetonitrile with stirring and under nitrogen. The reaction mixture rapidly turns an orange colour, and the solution is left to stir for 24 hours. After decantation and concentration by evaporating off, the solution is cooled overnight and small needle crystals form which correspond to the salicylic acid which has not reacted. The solution is refiltered, concentrated and cooled to 4° C. to give small yellow/orangey monoclinic crystals. After filtration and drying under vacuum, the compound of formula (III) is obtained with a yield of approximately 49%.

Melting point: 157–160° C. (decomposition)

The compounds of the invention have been the subject of biological studies which have demonstrated their properties of forming a glaze at the surface of the tooth and their value as substances for treating or preventing dental caries.

A fresh tooth sample is placed in a glass phial containing moist cotton and thymol at a temperature of +4° C.

The sample is cleared of soft tissues, possibly present on the tooth. The tooth is then polished in a rubber dish containing pumice stone free of fluoride, and then rinsed in an ultrasonic bath. The sample is treated with an aqueous solution of compound (III) of the invention, at pH 5, for 10 minutes at 37° C. The sample is then washed with water for one minute and a window made at the surface of the tooth is observed by microscopy.

The formation of an amorphous protective layer on the surface of the tooth after treatment of the sample with compound (III) is demonstrated.

The results of these biological tests show that the compounds of the invention exhibit properties of forming a protective glaze on the surface of the tooth.

They can be used in treating and preventing dental caries.

Examples of compositions of the invention are given below.

| Ingredient | Amount |
|---|---|
| Formulation for toothpaste. | |
| Titanium compound | q.s. 2500 ppm of F |
| Permethol | 0.250 g |
| 70% sorbitol | 25.00 g |
| Precipitated silicas | 18.00 g |
| Sodium lauryl sulphate | 2.00 g |
| Sodium carrageenate | 1.00 g |
| Titanium oxide | 1.00 g |
| Mint aroma | 0.950 g |
| Gesweet | 0.100 g |
| Parabens | 0.400 g |
| Water | q.s. 100,00 g |
| Titanium compound | q.s. 1500 ppm of F |
| Chlorhexidine digluconate | 0.125 g |
| Vitamin E acetate | 0.5 g |
| 70% sorbitol | 28.00 g |
| Precipitated silicas | 11.00 g |
| Sodium lauryl sulphate | 0.750 g |
| Chimexane NF | 0.750 g |
| Sodium carboxymethylcellulose | 1.300 g |
| Mint aroma | 1.00 g |
| Sodium saccharinate | 0.150 g |
| Titanium oxide | 1.00 g |
| Parabens | 0.300 g |
| Phosphate dodecahydrate | 0.070 g |
| Water | q.s. 100.00 g |
| Formulation for mouthwash. | |
| Titanium compound | q.s. 250 ppm of F |
| Sodium 4-methylesculetol monoethoxide | 1 g |
| D-panthenol | 5 g |
| Cremophor RH 410 | 0.5 g |
| 95% (V/V) alcohol | 80 g |
| Gesweet | 1 g |
| Mint aroma | 0.795 g |
| Patent blue | 0.004 g |
| Purified water | q.s. 1 000 g |
| Titanium compound | q.s. 250 ppm of F |
| Sodium benzoate | 0.4 g |
| 95% (V/V) alcohol | 10.00 g |
| Sodium saccharinate | 0.005 g |
| Benzoic acid | 0.100 g |
| Menthol aroma | 0.035 g |
| Levomenthol | 0.010 g |
| Dyes | 0.0012 g |
| Water | q.s. 100,00 g |

What is claimed is:

1. A titanium-derived compound having formula (I):

$$[TiF_xL_y]^{z-} \qquad (I)$$

in which L represents a compound of formula (II):

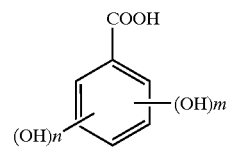

(II)

in which m is 1 and n is 0, 1 or 2 x represents 2, 4 or 5, y represents 1 or 2 and z represents 0, 1 or 2; or a pharmaceutically acceptable salt thereof.

2. A compound according to claim 1, wherein L is chosen from 2-hydroxybenzoic acid of formula:

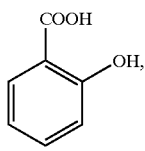

3-hydroxybenzoic acid of formula:

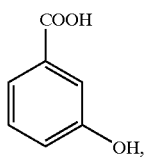

4hydroxybenzoic acid of formula:

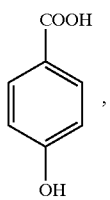

2,3dihydroxybenzoic acid of formula:

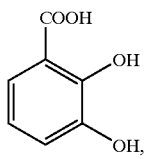

and 3,4-dihydroxybenzoic acid of formula:

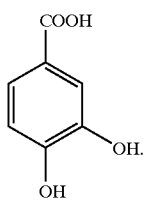

3. A compound according to claim 1 having formula (III):

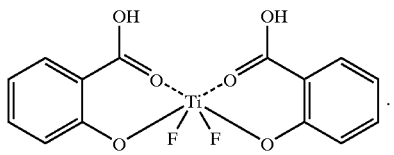

(III)

4. A method for preparing a titanium-derived compound according to claim 1 wherein solid titanium IV fluoride is reacted with a solution of benzoic acid in an anhydrous solvent under a nitrogen atmosphere.

5. A composition for buccal use comprising a titanium-derived compound having formula (I):

 (I)

in which L represents a compound of formula (II) below:

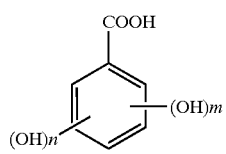

(II)

in which m is 0, 1 and n is 0, 1 or 2 x represents 2, 4 or 5, y represents 1 or 2 and z represents 0, 1 or 2; or a pharmaceutically acceptable salt thereof and a physiologically acceptable vehicle.

6. A composition according to claim 5 comprising a titanium-derived compound in an amount which is equivalent to from approximately 10 ppm to approximately 10,000 ppm of fluorine.

7. A composition according to claim 5 in the form of toothpaste or toothgel, of mouthwash, of spray, of foam, of gargling product, of dental gel or of chewing gum, balm, paste, glaze, lozenge, tablet, antiseptic throat preparation, powder, or concentrated or unconcentrated solution.

8. A composition according to claim 5 further comprising a polishing agent of inorganic or organic origin in proportions ranging up to 80% by weight with respect to the total weight of the composition.

9. A composition according to claim 8, wherein the polishing agent comprises calcium, magnesium or sodium carbonate or bicarbonate, calcium phosphates or sulphates, alumina or hydrated alumina, silicas, magnesium oxides, hydroxides, trisilicates or pyrophosphates, cellulose compounds obtained by crushing cereal seeds, sodium or potassium metaphosphates, calcium phosphate dihydrate, dicalcium phosphate, tricalcium phosphate, calcium pyrophosphate, aluminum or zirconium silicates, bentonite, magnesium orthophosphate or trimagnesium phosphate.

10. A composition according to claim 5 further comprising one or more cohesion agents, in proportions ranging up to approximately 10% by weight with respect to the total weight of the composition, chosen from natural thickeners, natural gums, guar, carob, carrageenan gums, synthetic carrageenates, and synthetic thickeners.

11. A composition according to claim 5 further comprising one or more surfactants of anionic, amphoteric, zwitterionic, cationic or nonionic nature.

12. A composition according to claim 5 further comprising one or more active agents used in buccal hygiene to reduce bad breath.

13. A composition according to claim 5 further comprising one or more cohesion agents, thickeners, antibiotics, wetting or refreshing agents, peptizing agents, preserving agents, sweeteners, dyes, aromas, flavourings or flavour-enhancing substances, plasticizers, antibacterial agents, vitamins, antitartar agents, healing agents, vasomotor agents, anti-bleeding agents, agents which are active on the gums, or anti-inflammatory agents.

14. A composition according to claim 13, wherein the sweetening agents comprise sucrose, lactose, fructose, xylitol, sodium cyclamate, sodium saccharinate or maltose, sodium or ammonium glycyrrhizinates, alpha-glucosyl/steviolglucoside mixtures, D-mannitol, aspartame, acesulfame K, sorbitol, lycosin or mixtures thereof.

15. A composition according to claim 13, wherein the antibacterial agents comprise essential oils, plant extracts, alexidine, octenidine, hexetidine, phenoxyethanol, phenethyl alcohol, triclosan, chlorhexidine, cetylpyridinium chloride or delmopinol, in proportions ranging up to approximately 10% by weight with respect to the total weight of the composition.

16. A method of protecting against dental caries which comprises administering a titanium-derived compound having formula (I):

$[TiF_xL_y]^{z-}$ (I)

in which L represents a compound of formula (II):

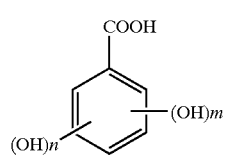
(II)

in which m is 0 or 1 and n is 0, 1 or 2,
x represents 2, 4 or 5, y represents 1 or 2 and z represents 0, 1 or 2; or
a pharmaceutically acceptable salt thereof.

17. A method for preparing a titanium-derived compound according to claim 2, wherein solid titanium IV fluoride is reacted with a solution of benzoic acid in an anhydrous solvent under a nitrogen atmosphere.

18. A method for preparing a titanium-derived compound according to claim 3, wherein solid titanium IV fluoride is reacted with a solution of benzoic acid in an anhydrous solvent under a nitrogen atmosphere.

19. A composition according to claim 6 in the form of toothpaste or toothgel, of mouthwash, of spray, of foam, of gargling product, of dental gel or of chewing gum, balm, paste, glaze, lozenge, tablet, antiseptic throat preparation, powder, or concentrated or unconcentrated solution.

20. A composition according to claim 6 further comprising a polishing agent of inorganic or organic origin in proportions ranging up to 80% by weight with respect to the total weight of the composition.

21. A composition according to claim 7 further comprising a polishing agent of inorganic or organic origin in proportions ranging up to 80% by weight with respect to the total weight of the composition.

22. A composition according to claim 19 further comprising a polishing agent of inorganic or organic origin in proportions ranging up to 80% by weight with respect to the total weight of the composition.

23. A composition according to claim 20, wherein the polishing agent comprises calcium, magnesium or sodium carbonate or bicarbonate, calcium phosphates or sulphates, alumina or hydrated alumina, silicas, magnesium oxides, hydroxides, trisilicates or pyrophosphates, cellulose compounds obtained by crushing cereal seeds, sodium or potassium metaphosphates, calcium phosphate dihydrate, dicalcium phosphate, tricalcium phosphate, calcium pyrophosphate, aluminum or zirconium silicates, bentonite, magnesium orthophosphate or trimagnesium phosphate.

24. A composition according to claim 21, wherein the polishing agent comprises calcium, magnesium or sodium carbonate or bicarbonate, calcium phosphates or sulphates, alumina or hydrated alumina, silicas, magnesium oxides, hydroxides, trisilicates or pyrophosphates, cellulose compounds obtained by crushing cereal seeds, sodium or potassium metaphosphates, calcium phosphate dihydrate, dicalcium phosphate, tricalcium phosphate, calcium pyrophosphate, aluminum or zirconium silicates, bentonite, magnesium orthophosphate or trimagnesium phosphate.

25. A composition according to claim 22, wherein the polishing agent comprises calcium, magnesium or sodium carbonate or bicarbonate, calcium phosphates or sulphates, alumina or hydrated alumina, silicas, magnesium oxides, hydroxides, trisilicates or pyrophosphates, cellulose compounds obtained by crushing cereal seeds, sodium or potassium metaphosphates, calcium phosphate dihydrate, dicalcium phosphate, tricalcium phosphate, calcium pyrophosphate, aluminum or zirconium silicates, bentonite, magnesium orthophosphate or trimagnesium phosphate.

26. A composition for buccal use comprising a compound according to claim 2.

27. A composition for buccal use comprising a compound according to claim 3.

28. A method of protecting against dental carries which comprises administering a compound according to claim 2.

29. A method of protecting against dental carries which comprises administering a compound according to claim 3.

30. A composition according to claim 10 wherein the cohesion agent is selected from the group consisting of alginates, pectins, gum tragacanth, xanthan, sodium carboxymethylcellulose, methylcellulose, hydroxyalkylcellulose, and crosslinked polyacrylic acids.

31. A composition according to claim 12 wherein the active agent used to reduce bad breath is selected from the group consisting of chlorhexidine, cetylpyridinium chloride, cyclodextrins, zinc halides, zinc acetate, zinc citrate, and zinc fluoride.

32. A composition according to claim 13 wherein the anti-inflammatory agent is selected from the group consisting of enoloxone, benzydamine, allantoin, and permethol.

* * * * *